(12) United States Patent
Miller et al.

(10) Patent No.: US 6,380,166 B1
(45) Date of Patent: Apr. 30, 2002

(54) GLUCOPYRANOSIDES CONJUGATES OF 2-(4-HYDROXY-PHENYL)-3-METHYL-1-[4-(2-AMIN-1-YL-ETHOXY)-BENZYL]-1H-INDOL-5-OLS

(75) Inventors: Chris P. Miller, Strafford; Michael D. Collini, Clifton Heights, both of PA (US); Bach D. Tran, Baltimore, MD (US); Anita Wai-Yin Chan, Fort Lee, NJ (US); Arkadiy Z. Rubezhov, West Nyack, NY (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/659,091

(22) Filed: Sep. 11, 2000

Related U.S. Application Data

(60) Provisional application No. 60/240,942, filed on Sep. 13, 1999.

(51) Int. Cl.[7] .......................... A61K 31/70; C07H 15/00
(52) U.S. Cl. ...................... 514/25; 536/17.4; 536/18.1
(58) Field of Search ................. 536/17.4, 18.1; 514/25

(56) References Cited

U.S. PATENT DOCUMENTS

| | | |
|---|---|---|
| 4,418,068 A | 11/1983 | Jones |
| 4,943,572 A | 7/1990 | Von Angerer |
| 5,023,254 A | 6/1991 | Von Angerer |
| 5,998,402 A | 12/1999 | Miller et al. |

FOREIGN PATENT DOCUMENTS

| | | |
|---|---|---|
| EP | 0639567 | 2/1995 |
| EP | 0683170 | 11/1995 |
| EP | 0802183 | 10/1997 |
| WO | 9310741 | 6/1993 |
| WO | 9517383 | 6/1995 |
| WO | 9603375 | 2/1996 |
| WO | 9924027 | 5/1999 |

OTHER PUBLICATIONS

Biberger et al., J. Steroid Biochem. Molec. Biol., 1996, 58(11), 31–43.
Nishino et al., J. Endocrinology, 1991, 130, 409–414.
Von Angerer et al., J. Med. Chem., 1990, 33, 2635–2640.
Von Angerer et al., J. Med. Chem., 1987, 30(1), 131.
Evans et al., Bone, 1995, 17(4), 181S–190S.

Primary Examiner—Elli Peselev
(74) Attorney, Agent, or Firm—Arnold S. Milowsky

(57) ABSTRACT

This invention provides tissue selective estrogens of formula I having the structure

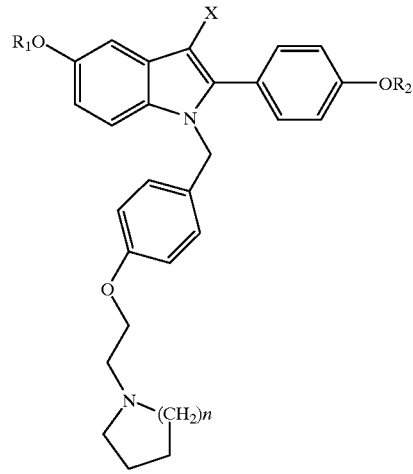

wherein:

$R_1$ and $R_2$ are independently, hydrogen, alkyl chain of 1–6 carbon atoms, benzyl, acyl of 2–7 carbon atoms, benzoyl,

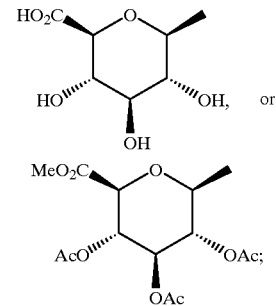

X is hydrogen, alkyl of 1–6 carbon atoms, CN, halogen, trifluoromethyl, or thioalkyl of 1–6 carbon atoms;

n=1–3;

with the proviso that at least one of $R_1$ or $R_2$ are not hydrogen, alkyl chain of 1–6 carbon atoms, benzyl, acyl of 2–7 carbon atoms, or benzoyl;

or a pharmaceutically acceptable salt thereof.

15 Claims, No Drawings

GLUCOPYRANOSIDES CONJUGATES OF 2-(4-HYDROXY-PHENYL)-3-METHYL-1-[4-(2-AMIN-1-YL-ETHOXY)-BENZYL]-1H-INDOL-5-OLS

This application claims the benefit of U.S. Provisional Application No. 60/240,942, which was converted from U.S. patent application Ser. No. 09/394,240, filed Sep. 13, 1999, pursuant to a petition filed under 37 C.F.R. 1.53(c)(2)(i).

BACKGROUND OF THE INVENTION

This invention provides glucopyranosides conjugates of 2-(4-hydroxy-phenyl)-3-methyl-1-[4-(2-amin-1-yl-ethoxy)-benzyl]-1H-indol-5-ols which are useful as tissue elective estrogenic agents.

The use of hormone replacement therapy for bone loss prevention in post-menopausal women is well precedented. The normal protocol calls for estrogen supplementation using such formulations containing estrone, estriol, ethynyl estradiol or conjugated estrogens isolated from natural sources (i.e., PREMARIN; conjugated equine estrogens). In some patients, therapy may be contraindicated due to the proliferative effects of unopposed estrogens (estrogens not given in combination with progestins) have on uterine tissue. This proliferation is associated with increased risk for endometriosis and/or endometrial cancer. The effects of unopposed estrogens on breast tissue are less clear, but are of some concern. The need for estrogens which can maintain the bone sparing effect while minimizing the proliferative effects in the uterus and breast is evident. Certain nonsteroidal antiestrogens have been shown to maintain bone mass in the ovariectomized rat model as well as in human clinical trials. Tamoxifen (sold as NOVALDEX, tamoxifen citrate), for example, is a useful palliative for the treatment of breast cancer and has been demonstrated to exert an estrogen agonist-like effect on the bone, in humans. However, it is also a partial agonist in the uterus and this is cause for some concern. EVISTA (raloxifene), a benzothiophene antiestrogen, has been shown to stimulate uterine growth in the ovariectomized rat to a lesser extent than Tamoxifen while maintaining the ability to spare bone. A useful review of tissue selective estrogens is seen in the article "Tissue-Selective Actions Of Estrogen Analogs", *Bone* Vol. 17, No. 4, October 1995, 181S-190S.

The use of indoles as estrogen antagonists has been reported by Von Angerer, See, J. Med. Chem. 1990, 33, 2635-2640; J. Med. Chem. 1987, 30, 131-136. Also see Ger. Offen., DE 3821148 A1 891228 and WO 96/03375.

WO A 95 17383 (Kar Bio AB) describes indole antiestrogens with long straight chains. Another related patent WO A 93 10741 describes 5-hydroxyindole with a generic descriptor incorporating other side chains. WO 93/23374 (Otsuka Pharmaceuticals, Japan) describes compounds which differ from the present invention; where $OR_2$ in the present formula I, below, is defined as thioalkyl and the reference discloses no such compounds having chains from the indole nitrogen having the same structure as the ones provided by the present invention. Where the side chain claimed is similar to that described herein, the compounds are amides: Acylated indoles are not claimed in the present invention. Glucuronic acid conjugates of the selective estrogen receptor modulator raloxifene (a benzothiophene) have been reported (EP 683170 A1 951122).

DESCRIPTION OF THE INVENTION

This invention provides compounds of Formula I having the structure

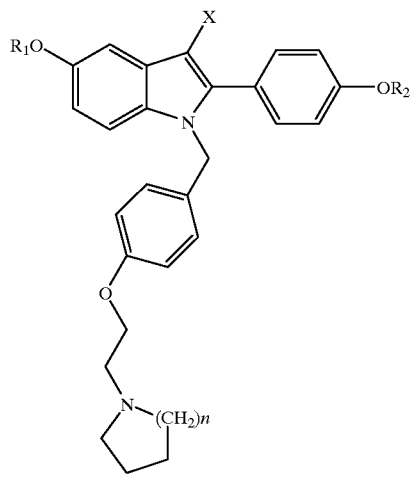

I wherein:
$R_1$ and $R_2$ are independently, hydrogen, alkyl chain of 1–6 carbon atoms, benzyl, acyl of 2–7 carbon atoms, benzoyl,

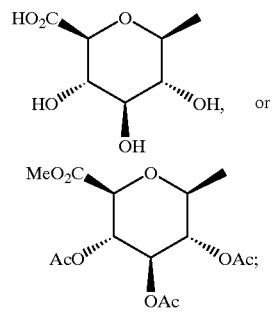

X is hydrogen, alkyl of 1–6 carbon atoms, CN, halogen, trifluoromethyl, or thioalkyl of 1–6 carbon atoms;
n=1–3;
with the proviso that at least one of $R_1$ or $R_2$ are not hydrogen, alkyl chain of 1–6 carbon atoms, benzyl, acyl of 2–7 carbon atoms, or benzoyl;
or a pharmaceutically acceptable salt thereof which are useful as tissue selective estrogens.

The alkyl moiety of the phenol ether substituent include both straight chain as well as branched moieties. Halogen means bromine, chlorine, fluorine, and iodine.

The pharmaceutically acceptable salts include salts formed from the addition reaction with either inorganic or organic acids. Inorganic acids such as hydrochloric acid, hydrobromic acid, hydroiodic acid, sulfuric acid, phosphoric acid and nitric acid are useful. Organic acids such as acetic acid, propionic acid, citric acid, maleic acid, malic acid, tartaric acid, phthalic acid, succinic acid, methanesulfonic acid, toluenesulfonic acid, napthalenesulfonic acid, camphorsulfonic acid and benzenesulfonic acid are also useful. The pharmaceutically acceptable salts of this invention also include quaternary ammonium salts which can be prepared by quaternizing the basic amine of the compounds of this invention with an electrophilic organic halide, mesylate, tosylate, and the like. Compounds of this invention which contain a carboxylic acid may form pharmaceutically acceptable base addition salts by treating the neutral starting material with a suitable inorganic base such as hydoxides or carbonates of alkali metals such as lithium, sodium, potassium, cesium, magnesium, calcium or barium. Or, the acid may be treated with an organic base (such as various organic primary (including ammonia), secondary or tertiary amines) to form the ammonium salts.

The compounds of this invention can be synthesized according to the generic methods shown in Scheme 1. The orthogonally protected indole is formed by a modified Bischler protocol wherein the α-bromo-4-pivaloyl protected hydroxypropiophenone or acetophenone 1 is reacted with 4-benzyloxyaniline in DMF in the presence of triethylamine. The reaction is monitored by TLC for consumption of starting materials. The aniline substituted material does not need to be isolated but instead, in the same flask, treated with an additional 1.25–1.5 equivalents of 4-benzyloxyaniline hydrochloride and heated to 120–160° C. until the previous intermediate is completely consumed. The protected indole 2 is subsequently treated with a suitable base such as sodium hydride in DMF and then reacted with an appropriate benzyl chloride of type 3. The indole 4 can then be mono-deprotected by either hydrogenating the benzyl group off at the 5-position of the indole or hydrolyzing the pivaloyl group at the 4'-position of the 2-phenyl group of the indole. The group removed is determined by the position of the glucuronic acid conjugate desired. The removal of the benzyl group or the pivaloyl ester renders compounds of either type 5 or 6, respectively. Reaction of compound 5 or 6 with the trichloroacetimidate CAS# [150607-95-7] of the protected glucopyranoside in the presence of BF$_3$ etherate in a polar aprotic solvent such as dichloromethane results in the glucopyranisodated compounds 7 or 8. We have found that the reaction of either 7 or 8 with the trichloroacetimidate supra in CH$_2$Cl$_2$ using 3 Å molecular sieves allowed for the synthesis of the glucopyranosides in very good yield. The compounds are exclusively formed as the β-glucopyranosides (equatorial substituted). The pivaloylated compound 7 can be then treated with LiOH in THF/H$_2$O/MeOH (or dioxane/MeOH/H$_2$O) to effect the complete deprotection of the compound, to give after workup, the monoglucuronic acid 9. The mono-benzyl ether 8 can be hydrogenated by hydrogen transfer between cyclohexadiene and Pd/C and then hydrolyzed by LiOH in THF/H$_2$O/MeOH (or dioxane/MeOH/H$_2$O) to yield the mono glucuronic acid 10. More preferable for larger scale hydrogenations are the conditions using a 10% Pd/C catalyst, H$_2$ and a solvent system consisting of THF/EtOH.

Scheme 1

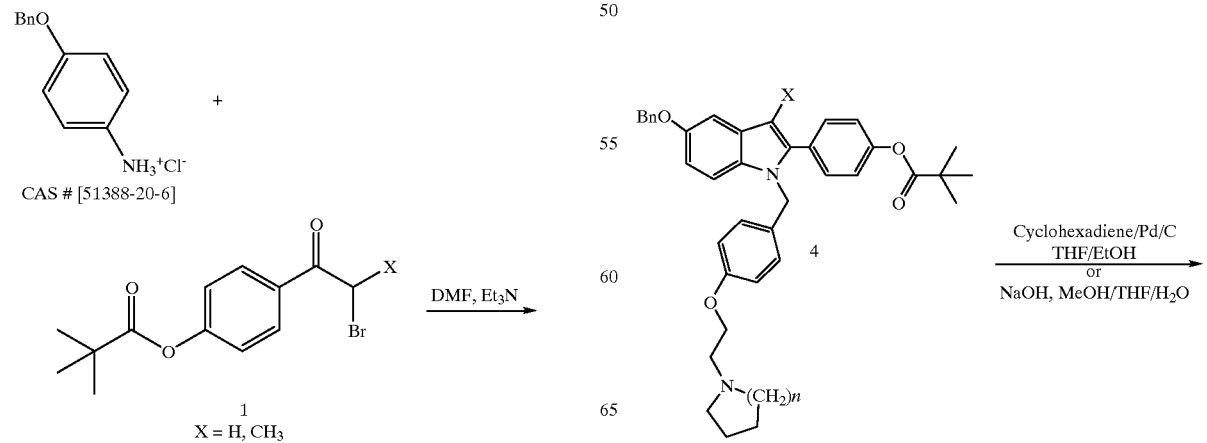

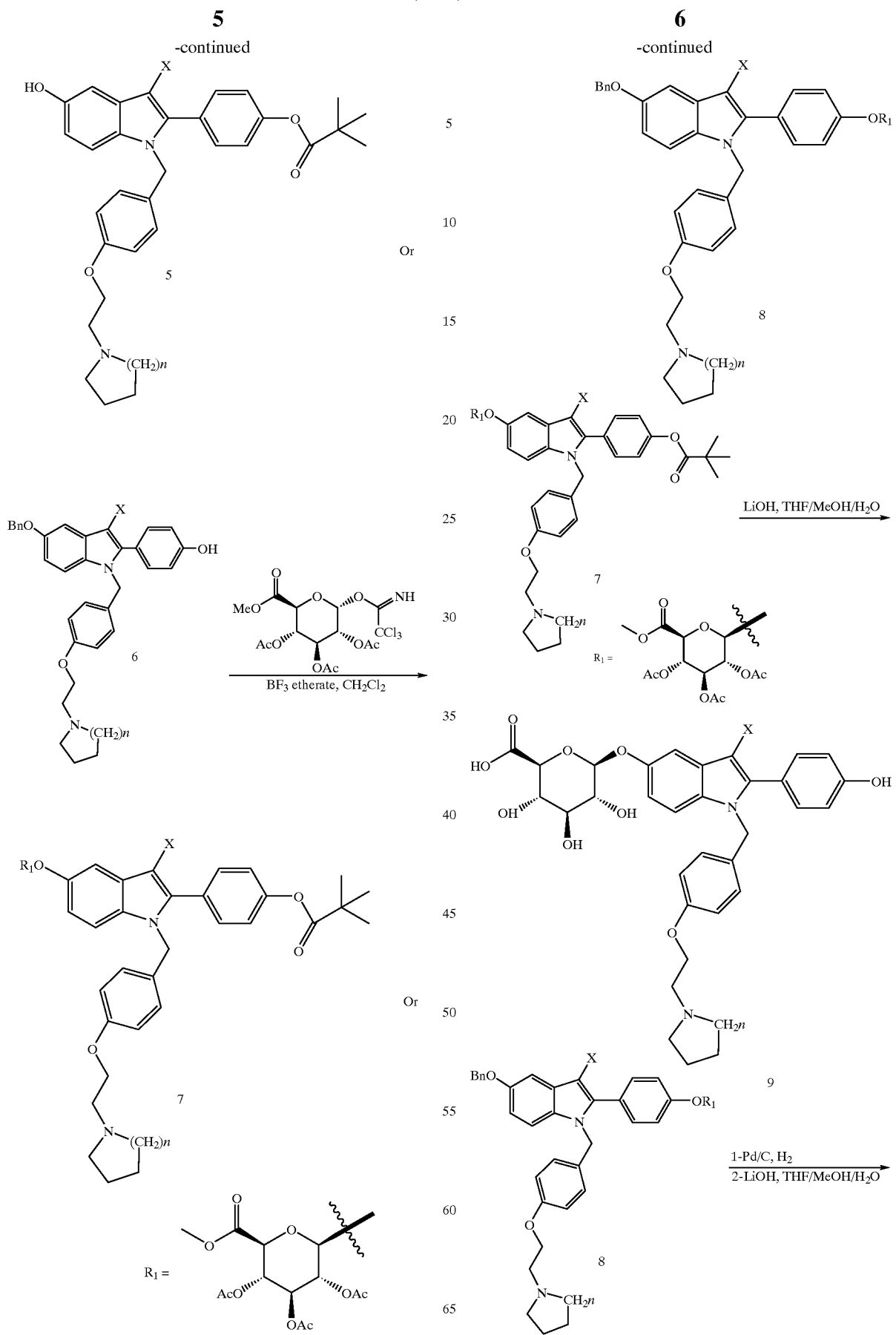

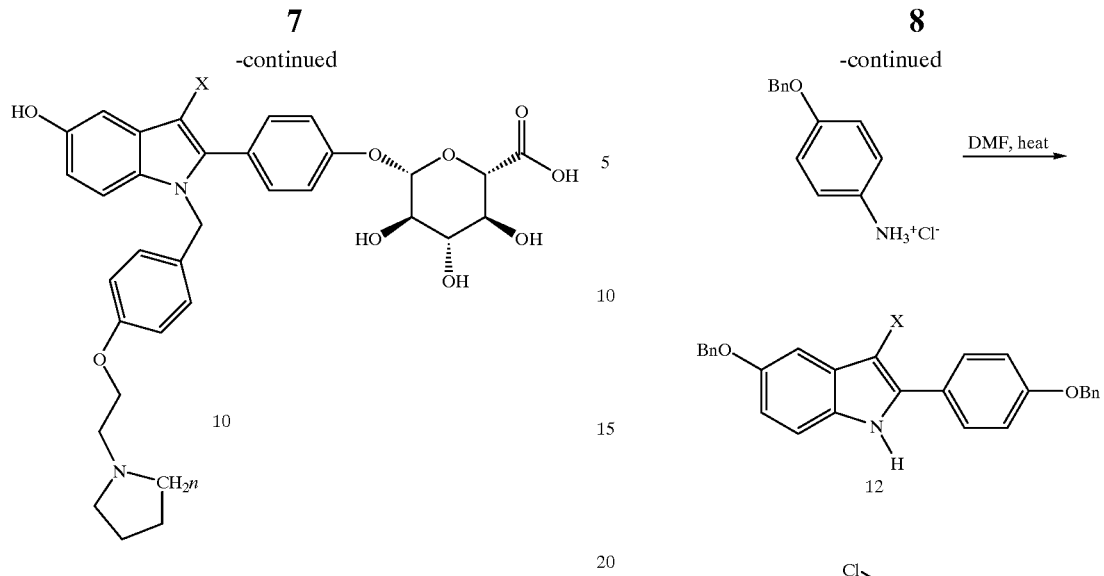

Compounds wherein both phenols are glucuronidated can be prepared according to Scheme 2. The bis-benzyl protected indole 12 is prepared by a modified Bischler reaction analogously to that described for indole 2 in scheme 1. The indole can then be subsequently alkylated with the side chain 3 (same as shown in scheme 1). The substituted indole 13 can then be deprotected by hydrogenation of the benzyl ethers to form the deprotected compound 14. The deprotected compound is then bis-glucuronidated by treatment of the free phenolic containing compound with the trichloroacetimidate of the protected glucopyranoside CAS# [150607-95-7] (same reagent used as in scheme 1) to afford 15. The final deprotected bis-glucuronic acid is obtained by base hydrolysis of precursor 15 to afford product 16. The side chains can be prepared in the general fashion shown in Scheme 3.

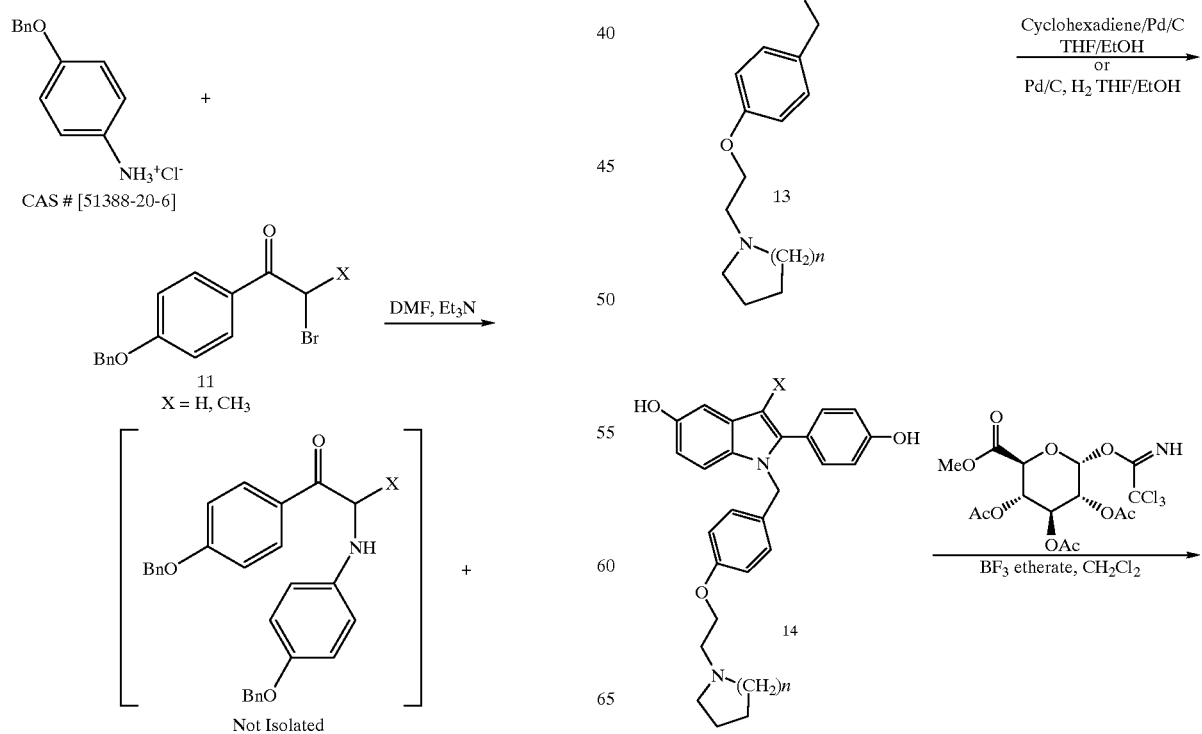

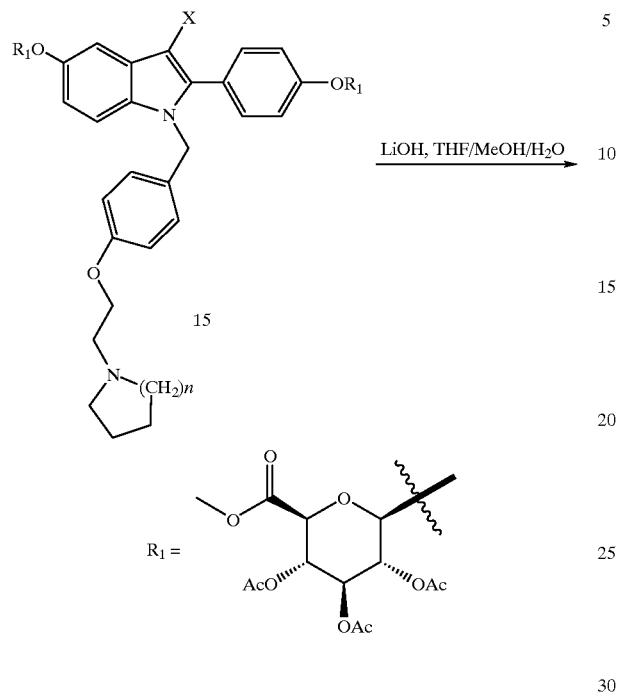
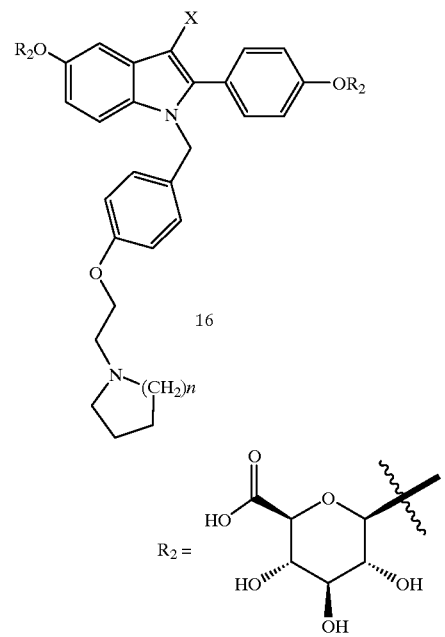
Scheme 3
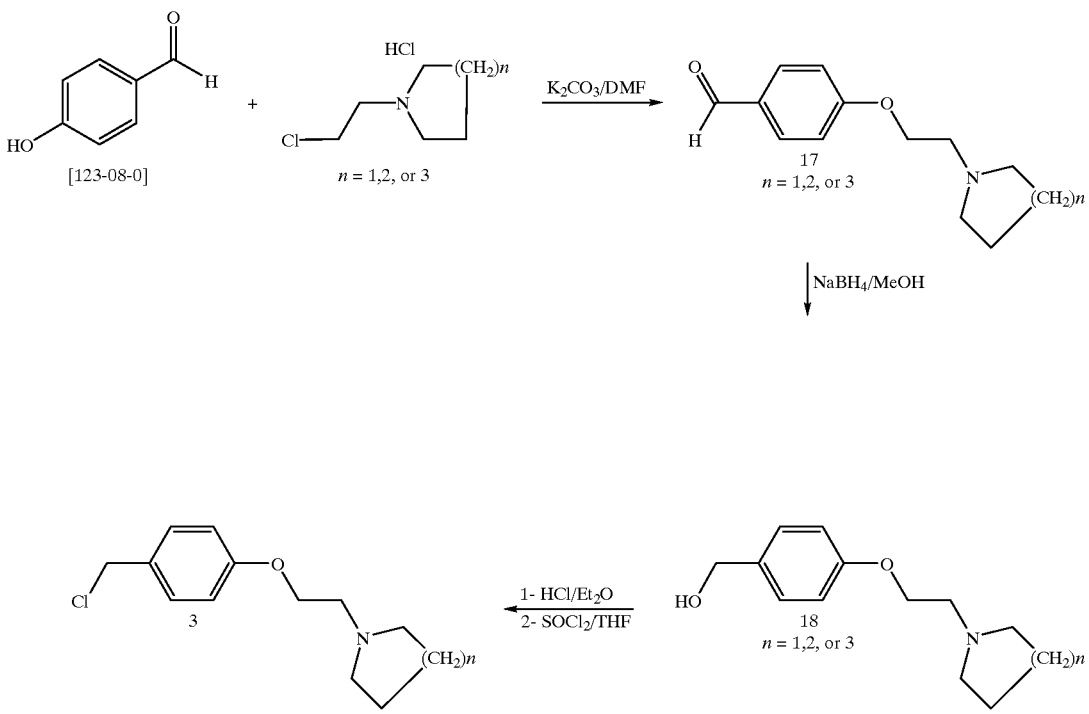

Estrogen antagonist activity was shown for representative compounds of this invention in a standard pharmacological test procedure using MCF-7 cells transfected with an estrogen receptor. When administered orally, the compounds of this invention act at least partially as prodrugs for the corresponding hydroxylated compounds disclosed in EP 802183. Accordingly, the compounds of this invention are tissue selective estrogens, meaning that in certain tissue containing estrogen receptors, the compounds will act as estrogen agonists, and in other tissue containing estrogen receptors, the compounds will act as antagonists. The procedure used to demonstrate the estrogen antagonist activity in MCF-7 carcinoma cells is briefly summarized below, and the results obtained are provided in Table 1.

Cell Preparation: MCF-7 cells were passaged twice a week with growth medium [D-MEM/F-12 medium containing 10% (v/v) heat-inactivated fetal bovine serum, 1% (v/v) Penicillin-Streptomycin, and 2 mM glutaMax-1]. The cells were maintained in vented flasks at 37° C. inside a 5% C)2/95% humidified air incubator. One day prior to treatment, the cells were plated with growth medium at 25,000/well into 96 well plates and incubated at 37° C. overnight.

Test Procedure Conditions: The cells were infected for 2 h at 37° C. with 50 uL/well of a 1:10 dilution of adenovirus 5-ERE-tk-luciferase in experimental medium [phenol red-free D-MEM/F-12 medium containing 10% (v/v) heat-inactivated charcoal-stripped fetal bovine serum, 1%(v/v) Penicillin-Streptomycin, 2 mM gluta-Max-1, 1 mM sodium pyruvate]. The wells were washed once with 150 uL of experimental medium. Finally, the cells were treated for 24 h at 37° C. in replicates of 8 wells/treatment with 150 uL/well of vehicle (< or equal to 0.1% v/v DMSO) or compound that was diluted > or equal to 1000 fold into experimental medium.

Dose response experiments were performed in either the agonist or antagonist modes on active compounds in log increases from $10^{-14}$ to $10^{-5}$ M. From these dose-response curves, $EC_{50}$ and $IC_{50}$ values, respectively, were generated. The final well in each treatment group contains 5 uL of $3\times10^{-5}$ ICI-182,780 ($10^{-6}$ M final concentration) as an ER antagonist control.

After treatment the cells were lysed on a shaker for 15 min with 25 uL/well of 1× cell culture lysis reagent (Promega Corporation). The cell lysates (20 uL) were transferred to a 96 well luminometer plate, and luciferase activity was measured in a MicroLumat LB 96 P luminometer (EG and G Bethold) using 100 uL/well of luciferase substrate (Promega Corporation). Prior to the injection of the substrate, a 1 second background measurement was made for each well. Following the injection of the substrate, luciferase activity was measured for 10 seconds after a 1 second delay. The data were transferred from the luminometer to a Macintosh personal computer and analyzed using the JMP software (SAS institute); this program subtracts the background reading from the luciferase measurement for each well and then determine the mean and standard deviation of each treatment.

Analysis of Results: The luciferase data were transformed by logarithms, and the Huber M-estimator was used to down-weight the outlying transformed observations. The JMP software was used to analyze the transformed and weighted data for one-way ANOVA (Dunnet's test). The compound treatments were compared to the vehicle control results (0.1 nM 17β-estradiol) in the antagonist mode. For the initial single dose experiment, if the compound treatment results were significantly different from the appropriate control ($p<0.05$), then the results were reported as the percent relative to the 17β-estradiol control [i.e., ((compound-vehicle control)/(17β-estradiol control—vehicle control))×100]. The JMP software was also used to determine the $EC_{50}$ and/or $IC_{50}$ values from the non-linear dose-response curves.

The mono-glucuronic acid conjugates were tested in the MCF-7 assay in both the agonist as well as the antagonist (co-dosed with 10 pM 17β-estradiol) modes. All four compounds tested showed antiestrogenic activity in this cell system and none of the compounds showed significant agonist activity in these cells. This is a desirable outcome since the MCF-7 cell line is derived from human mammary tissue and these results indicate that the compounds were counteracting the proliferative effects of estrogen activity in these cells. This also is a positive indication in that these compounds are showing cell permeability and receptor binding affinity (since the MCF-7 cells express estrogen receptors). The data for the compounds is shown in Table 1 infra.

TABLE 1

| Compound # | MCF-7 $IC_{50}$ |
|---|---|
| 29 (Scheme 5) | 230 nM |
| 30 (Scheme 5) | 210 nM |
| 37 (Scheme 6) | 1200 nM |
| 38 (Scheme 6) | 1100 nM |

As stated above, the compounds of this invention are tissue selective estrogens: acting as estrogen agonists on certain tissue, and antagonists on other tissue. In particular, the compounds of this invention act as estrogen receptor agonists in providing protection against osteoporisis, lowering lipid levels, and increasing HDL levels. The compounds of this invention act as estrogen receptor antagonists in inhibiting uterine growth (as a potential side effect from the administration of estrogenic compounds), provide protection against breast cancer, provide contraception, inhibit dementias, and provide cognition enhancement.

Accordingly, the compounds of this invention are useful in treating certain conditions resulting from estrogen deficiency, such as bone loss or osteoporosis which may have resulted from an imbalance in an individual's formation of new bone tissues and the resorption of older tissues, leading to a net loss of bone. Bone depletion results in a range of individuals, particularly in post-menopausal women, women who have undergone bilateral oophorectomy, those receiving or who have received extended corticosteroid therapies, those experiencing gonadal dysgenesis, and those suffering from Cushing's syndrome. These compounds may also address individuals with special needs for bone, including teeth and oral bone, replacement, bone fractures, defective bone structures, individuals having bone-related surgeries and/or the implantation of prosthesis. In addition to those problems described above, these compounds can be used in treatments for osteoarthritis, hypocalcemia, hypercalcemia, Paget's disease, osteomalacia, osteohalisteresis, multiple myeloma and other forms of cancer having deleterious effects on bone tissues. Other conditions resulting from estrogen deficiency which can be treated with compounds of this invention include prostatic hypertrophy, vaginal and skin atrophy, acne, cardiovascular disease, contraception in pre-menopausal women, as well as hormone replacement therapy in post-menopausal women or in other estrogen deficiency states where estrogen supplementation would be beneficial.

As the compounds of this invention also act as estrogen antagonists in certain tissue, they are useful in providing antiestrogen therapy, particularly in treating male pattern baldness, dysfunctional uterine bleeding, endometrial polyps, benign breast disease, uterine leiomyomas, adenomyosis, in treating neoplasms such as ovarian cancer, breast cancer, endometrial cancer, melanoma, prostrate cancer, cancers of the colon, and CNS cancers, in treating endometriosis, polycystic ovary syndrome, infertility Alzheimer's disease, cognitive decline and other CNS disorders, and in providing contraception. The compounds of this invention are also useful in treating disease states where amenorrhea is advantageous, such as leukemia, endometrial ablations, chronic renal or hepatic disease or coagulation diseases or disorders.

Additionally, compounds 27, 28, 33, and 34 are intermediates useful in the preparation of compounds 29, 30, 35, 36, 37, and 38 as shown in Schemes 5 and 6 (below).

Effective administration of these compounds may be given at a dose of from about 0.1 mg/day to about 1,000 mg/day. Preferably, administration will be from about 10 mg/day to about 600 mg/day, more preferably from about 50 mg/day to about 600 mg/day, in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, as suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, , xanthan gum, sodium citrate, complex silicates, calcium carbonate, glycine, dextrin, sucrose, sorbitol, dicalcium phosphate, calcium: sulfate, lactose, kaolin, mannitol, sodium chloride, talc, dry starches and powdered sugar. Oral formulations herein may utilize standard delay or time release formulations to alter the absorption of the active compound(s). Suppository formulations may be made from traditional materials, including cocoa butter, with or without the addition of waxes to alter the suppository's melting point, and glycerin. Water soluble suppository bases, such as polyethylene glycols of various molecular weights, may also be used.

It is understood that the dosage, regimen and mode of administration of these compounds will vary according to the malady, the individual being treated, and subject to the judgement of the medical practitioner involved. It is preferred that the administration of one or more of the compounds herein begin at a low dose and be increased until the desired effects are achieved.

The following procedures describe the preparation of representative examples of this invention.

All reactions were carried out under a nitrogen atmosphere. Chromatography was performed using 230–400 mesh silica gel. Thin layer chromatography was performed with silica gel plates. $^1$H NMR spectra were obtained on a Bruker AM-400, GE QE 300, Bruker DPX-300 or DPX-301 instrument and chemical shifts reported in ppm. Melting points were determined on a Thomas-Hoover apparatus and are uncorrected. IR spectra were recorded on a Perkin-Elmer diffraction grating, Mattson 5020FT-IR or Perkin-Elmer 784 spectrophotometers. Mass spectra were recorded on a Kratos MS 50 or Finnigan 8230 mass spectrometers. LC/MS were preformed on a Micromass system, Model Platform LC with a HP 1100 LC system and a Diode Array detector. The column used was a 2.0×50 mm C18 3 µm column. The mobile phase used were as followed: A=950 (10 mM NH$_4$OAc): 50 (CH$_3$CN); B=50 (10 mM NH$_4$OAc):950 (CH$_3$CN). The gradient used is as followed, t=0, 100% A, 0% B; t=15, 0% A, 100% B. BPLC were recorded on a Waters 60F Pump HPLC system with a 4.6 mm×15 cm LUNA 3 µm, C18 column and a 996 Diode Array detector (at 300 nm or 220 nm). Flow=1.0 mL/min. Temp=30° C. The mobile phase used were as followed: A=950 H$_2$O:50 CH$_3$CN, 20 mM K$_2$HPO$_4$/H$_3$PO$_4$; B=300 H$_2$O:700 CH$_3$CN, 20 mM K$_2$HPO$_4$/H$_3$PO$_4$. The gradient used is as followed, t=0, 100% B, 0% C; t=55, 0% B, 100% C. Elemental analyses were obtained with a Perkin-Elmer 2400 elemental analyzer. Compounds for which CHN are reported are within 0.4% of the theoretical value for the formula given unless expressed otherwise.

The following compounds [Examples 1–3] were prepared according to Scheme 4 as shown below.

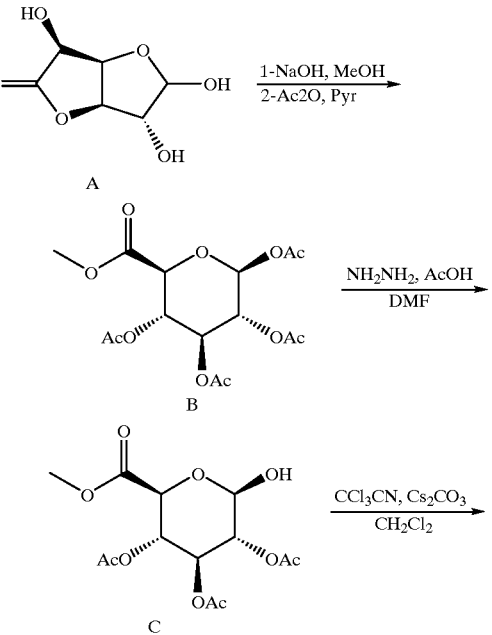

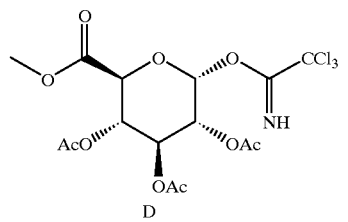

Scheme 5

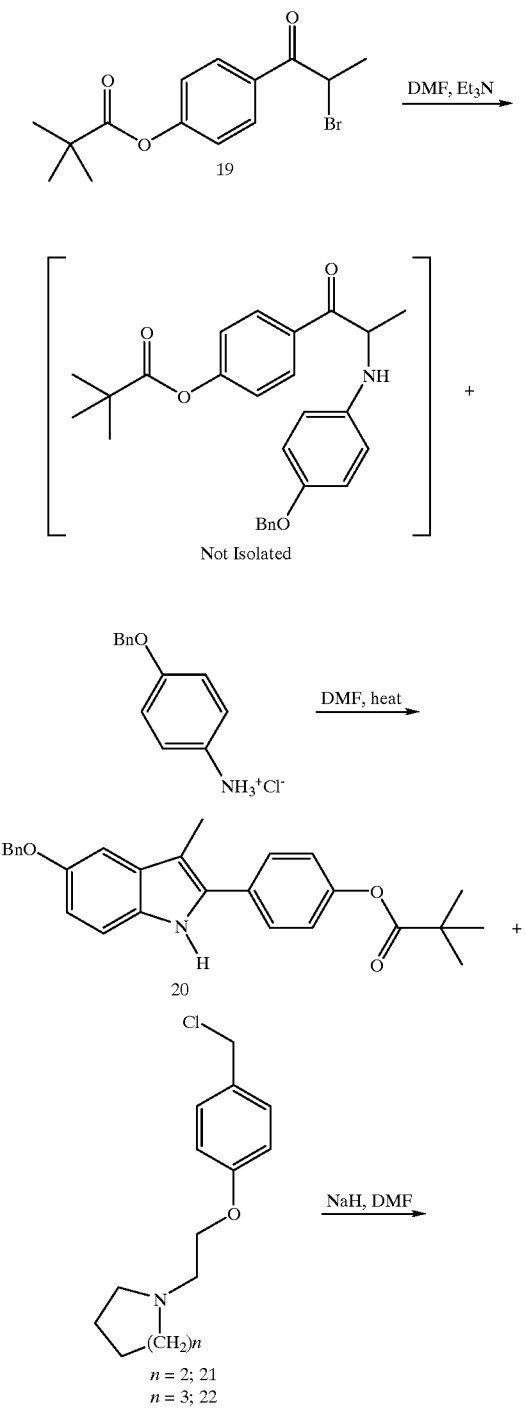

EXAMPLE 1

Formation of Tetraacetylglucuronic Ester B

To a suspension of D-Glucuronolactone A (100 g, 56.8 mmol, available from Aldrich Chemical) in MeOH (750 mL) was added NaOH pellets (0.4 g, 0.01 mmol) under Ar. The suspension slowly turned to a clear yellow solution over 2 h of stirring. After 16 h, the reaction mixture was concentrated in vacuo to give a brown foam. The crude product was dissolved in pyridine (200 mL), cooled in an ice-bath before acetic anhydride (375 mL) was added in 50-mL portions. The reaction turned dark brown during addition. After addition, the reaction mixture was purged with Ar and stored in the refrigerator. After 36 h, a brownish precipitate formed on the bottom of the flask. The reaction mixture was filtered and washed with warm EtOH (100 mL), air-dried overnight to give B 78.5 g, 37% of an off-white solid: $R_f$=0.65 (EtOAc); $^1$H NMR (CDCl$_3$) 5.77 (d, 1H, J=7.7 Hz), 5.12–5.35 (m, 3H), 4.18 (d, 1H, J=9.3 Hz), 3.75 (s, 3H), 2.04–2.12 (m, 12H).

EXAMPLE 2

Formation of Hydroxyglucuronic Ester C

To a solution of tetraacetylglucuronic ester B in DMF (90 mL) was added solid hydrazine acetate (3 g, 32.6 mmol) at rt under Ar. The suspension was heated to 65° C. under Ar. After 1 h, the reaction was cooled to rt, poured into H$_2$O (200 mL) and EtOAc (200 mL). The two layers were separated. The organic layer was extracted with H$_2$O (2×150 mL), dried over Na$_2$SO$_4$, filtered, concentrated in vacuo. Purification via SiO$_2$, eluted with (2:1) hexanes:EtOAc gave 4.1 g, 46% yield of hydroxyglucuronic ester C as a yellow syrup. $R_f$=0.61 (EtOAc); $^1$H NMR (CDCl$_3$) 4.58–5.63 (m, 4H), 3.75 (s, 3H), 1.97–2.22 (m, 9H).

EXAMPLE 3

Formation of Trichloroacetimidate D

To a solution of hydroxyglucuronic ester C (11.1 g, 33.3 mmol) in CH$_2$Cl$_2$ (100 mL) was added cesium carbonate (1.5 g, 4.7 mmol) and trichloroacetonitrile (10 mL, 63 mmol) at rt under Ar. After 4 d of stirring, H$_2$O (200 mL) and CHCl$_3$ (100 mL) were added to the suspension. The two layers were separated. The organic layer was extracted with H$_2$O (2×100 mL), dried over Na$_2$SO$_4$, filtered, concentrated in vacuo. Purification via SiO$_2$, eluted with (1:1) hexanes:EtOAc gave 8.9 g, 58% of trichloroacetimidate D as an off-white solid. $R_f$=0.67 (EtOAc); $^1$H NMR (CDCl$_3$) 8.78 (s, N-H), 6.63 (m, 1H), 5.63 (t, 1H, J=9.86 Hz), 5.27 (t, 1H, J=10.0 Hz), 5.15 (dd, 1H, J=3.54, 10.2 Hz), 4.50 (d, 1H, J=10.2 Hz), 3.68 (s, 3H), 2.02–2.12 (m, 9H).

The following 5-glucopyranoside conjugates and intermediates [Examples 4–21] were prepared according to Schemes 5 and 6 as shown below.

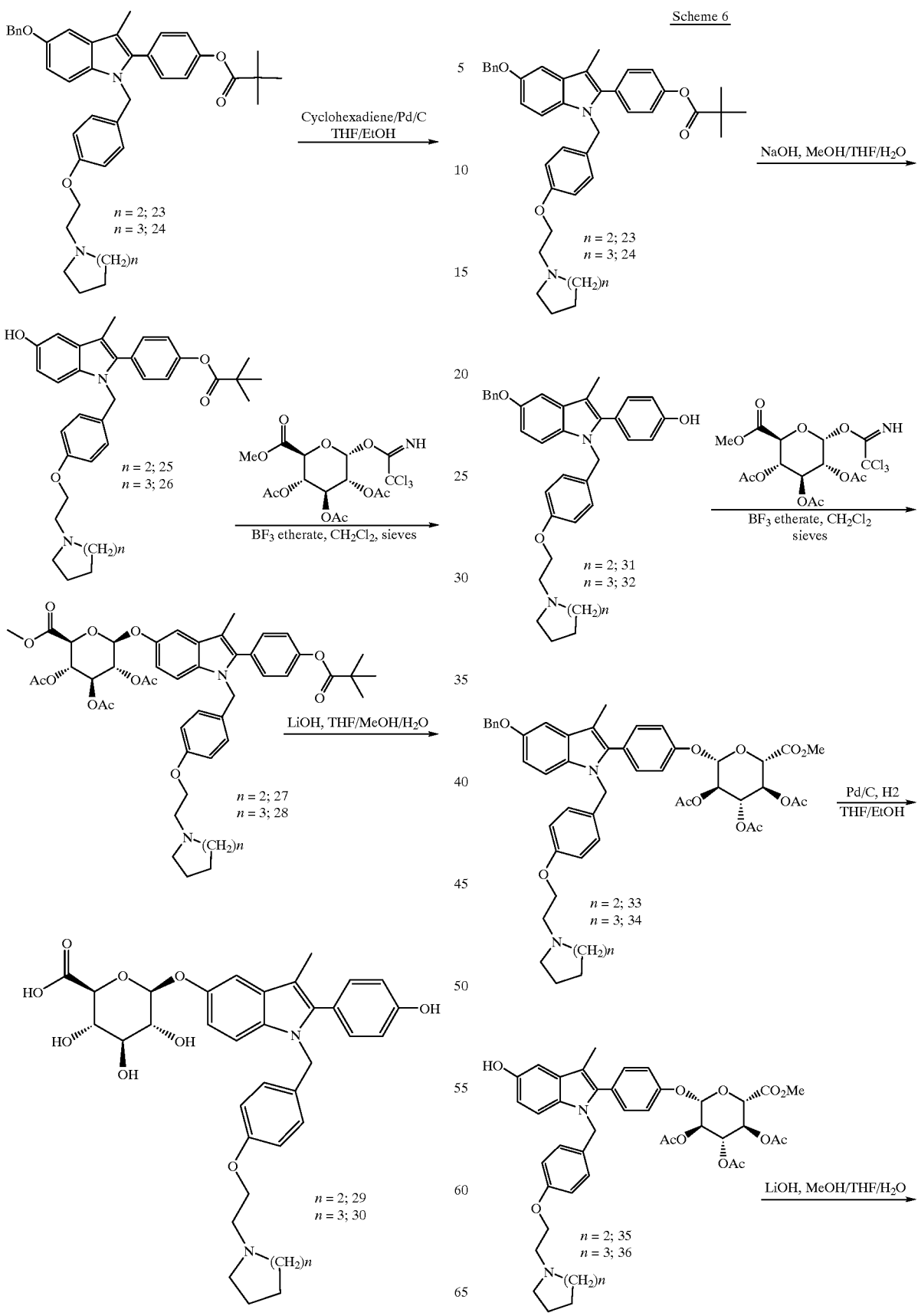

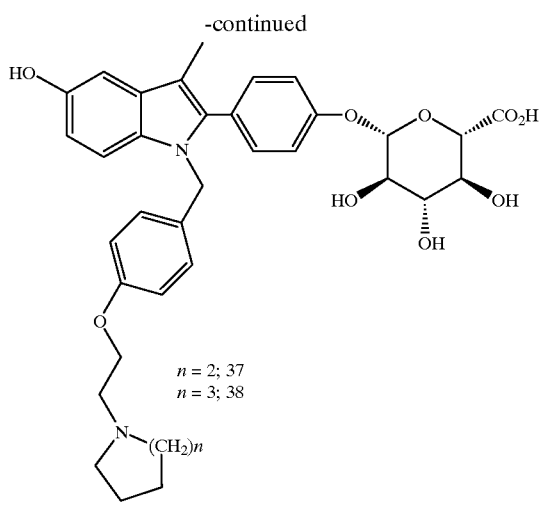

n = 2; 37
n = 3; 38

EXAMPLE 4
Propanoic Acid, 2.2-Dimethyl-, 4-(1-oxo-2-bromo-propyl) phenyl Ester (19)

To a dilute solution of the 4'-pivalolyl propiophenone (22.4 g, 95.6 mmol) in ether (1.2 L) at 0° C. was added slowly $Br_2$ (16.7 g, 105.2 mmol). The reaction was run at 0° C. for 20 min and then allowed to room temperature for 45 min. The gradual disappearance of the bromine color was observed as the reaction went on at rt. The product has the same rf as the starting material in the TLC system 10% EtOAc/Hex. The reaction was quenched with 10% solution of $Na_2SO_3$, washed with water, brine, and dried over $MgSO_4$. The product is a waxy solid and was used in the next step without purification (yield=30 g, 100%). mp=40–45° C.

EXAMPLE 5
2,2-Dimethyl-propionic Acid 4-(5-benzyloxy-3-methyl-1H-indol-2yl)phenyl Ester (20)

A solution of DMF (350 mL) containing bromo ketone 19 (44.82 g, 143 mmol), para-benzyloxy aniline hydrochloride (37.1 g, 157.4 mmol, 1.1 eq), $Et_3N$ (31.85 g, 314.8 mmol, 2.2 eq) was heated to 130° C. for 1.5 h and the rxn followed by TLC (15% EtOAc/Hex). The intermediate product α-anilino propiophenone was observed as a more polar spot than the α-bromo 4'-pivaloyl propiophenone. After all of the starting material was consumed, at 130° C. the reaction solution was treated with additional para-benzyloxy aniline hydrochloride (42 g, 177 mmol). The reaction mixture was then heated for an additional 3.5 h at 130° C. The reaction mixture was allowed to come to rt, washed with water (800 mL), extracted by EtOAc (3×300 mL), washed with brine, and dried over with $MgSO_4$. The organic layer was concentrated to give a crude product which was triturated with MeOH (3 times) to give a white solid (38 g, 64%): Mp=156–158° C.; $^1$H NMR (DMSO) 11.0 (s, 1 H), 7.67 (d, 2 H, J=8.6 Hz), 7.49 (d, 2 H, J=7.1 Hz), 7.43–7.29 (m, 3 H), 7.28–7.19 (m, 3 H), 7.12 (d, 1 H, J=2.3 Hz), 6.83 (dd, 1 H, J=8.7 Hz, 2.3 Hz), 5.13 (s, 2 H), 2.37 (s, 3 H), 1.33 (s, 9 H); MS 414 (M+H)+; IR (KBr) 3380, 2970, 1745 cm$^{-1}$.

EXAMPLE 6
2,2-Dimethyl-propionic Acid 4-{5-benzyloxy-3-methyl-1-[4-(2-piperidin-1-yl-ethoxy)-benzyl]-1H-indol-2-yl}-phenyl Ester (23)

To a slurry of NaH (11.7 g, 60% dispersion in mineral oil, 0.292 mol, 2.5 eq) in DMF (500 mL) at −25° C. was added dropwise a solution of the 1-unsubstituted indole precursor 20 (48.3 g, 0.117 mol, 1 eq) in DME (500 mL) over a period of 50 min, and the reaction allowed to continue for an hour at −25° C. for an additional hour. The indole anion was then treated with a dropwise addition of a solution consisting of the side chain 21 (51.0 g, 0.176 mol, 1.5 eq) in DMF (500 mL) over a period of 55 minutes during which time the solution temperature was maintained at −25° C. The reaction was allowed to stir for an additional hour at −25° C. followed by 24 h at rt. The reaction mixture was diluted with EtOAc (1.2 L), washed with brine (8×300 mL), dried over $Na_2SO_4$ and concentrated to give 92.8 g of a brown oil which was dissolved in the minimum amount of $CH_2Cl_2$ and chromatographed on silica gel (1 Kg) with $CH_2Cl_2$, then $CH_2Cl_2$/MeOH 98:2 and finally $CH_2Cl_2$/MeOH 96:4. The fraction eluted with $CH_2Cl_2$ contained unreacted starting material (14.5 g), and the eluant from the $CH_2Cl_2$/MeOH fractions was concentrated to give the desired product (36.7 g, 70%). $^1$H NMR (DMSO) 7.52–7.45 (m, 2 H), 7.43–7.36 (m, 4 H), 7.35–7.31 (m, 1 H) 7.28–7.20 (m, 3 H), 7.15 (d, 1 H, J=2.3 Hz), 6.84 (dd, 1 H, J=8.9 Hz, 2.4 Hz), 6.73 (s, 4 H), 5.18 (s, 2 H), 5.13 (s, 2 H), 3.94 (t, 2 H, J=5.9 Hz), 2.56 (t, 2 H, J=5.9 Hz), 2.41–2.35 (m, 4 H), 2.18 (s, 3 H), 1.51–1.42 (m, 4 H), 1.32 (s, 11 H); IR (KBr) 3410 ($H_2O$), 2930, 1750; MS 631.

EXAMPLE 7
2,2-Dimethyl-propionic Acid 4-{5-benzyloxy-3-methl-1-[4-(2-hexamethyleneamine-1-yl-ethoxy)-benzyl]-1H-indol-2-yl}-phenyl Ester HCl (24)

The indole 20 (2.0 g, 4.84 mmol) was dissolved in DMF and cooled to 0° C. and treated with NaH (0.13 g, 5.32 mmol as a 60% dispersion in mineral oil). A separate flask containing the benzyl chloride 22 (2.0 g, 6.57 mmol) in DMF was treated with NaH (0.17 g, 7.22 mmol as a 60% dispersion in mineral oil) at 0° C. The solution containing the benzyl chloride was then transferred via syringe to the solution containing the indole anion. The reaction was maintained at 0° C. for 0.5 h then allowed to rt and stirred for an additional 5 h. The reaction was worked up by partitioning the reaction mixture between water and EtOAc and washing the EtOAc with brine and drying over $MgSO_4$. The solution was concentrated and chromatographed on $SiO_2$ (MeOH/$CH_2Cl_2$; 5:95) to yield the desired pdt as a foam (0.41 g). The foam was treated with a 1N HCl solution in $Et_2O$ to render the product as a light yellow solid. Mp=222–225° C.; $^1$H NMR (DMSO) 10.17 (br s, 1 H), 7.95–7.22 (m, 10 H), 7.16 (d, 1 H, J=2.3 Hz), 6.87–6.76 (m, 5 H), 5.22 (s, 2 H), 5.13 (s, 2 H), 4.27 (t, 1 H, J=4.6 Hz), 3.47–3.37 (m, 4 H), 3.20–3.16 (m, 2 H), 2.19 (s, 3 H), 1.85–1.73 (m, 4 H), 1.66–1.53 (m, 4 H), 1.32 (s, 9 H); MS (+) APCI 645 (M+H$^+$).

EXAMPLE 8
2,2-Dimethyl-propionic Acid 4-{5-hydroxy-3-methyl-1-[4-(2-piperidin-1-yl-ethoxy) benzyl]-1H-indol-2-yl}-phenyl Ester (25)

The protected indole 23 (61.8, 0.098 mol) was dissolved in THF/EtOH (0.35 L/0.35 L), and 10% Pd/C (7.0 g) was added. The mixture was then hydrogenated at rt in a Parr apparatus at 50 psI for 30 h. The reaction was then filtered through Siluflock and 0.62 g of ascorbic acid was added to the filtrate to minimize any potential oxidation. The cake of Siluflock was washed with THF and the combined filtrates were concentrated to render a white solid which was washed with hexanes and dried to give 44.5 g of 25 (84%) as a white solid.

$^1$H NMR (DMSO) 8.76 (s, 1 H), 7.40 (d, 2 H, J=8.0 Hz), 7.22 (d, 2 H, J=7.8 Hz), 7.14 (d, 1 H, J=8.7 Hz), 6.84 (d, 1

H, J=1.6 Hz), 6.76–6.72 (m, 4 H), 6.63 (dd, 1 H, J=8.7 Hz, 1.4 Hz), 5.14 (s, 2 H), 3.94 (t, 2 H, J=5.8 Hz), 2.57 (t, 2 H, J=6.0 Hz), 2.42–2.33 (m, 4 H), 2.14 (s, 3 H), 1.50–1.39 (m, 4 H), 1.32 (s, 11 H); IR (KBr) 3400, 2900, 1750 cm$^{-1}$; MS 540.

EXAMPLE 9

2.2-Dimethyl-propionic Acid 4-{5-hydroxy-3-methyl-1-[4-(2-azepan-1-yl-ethox) benzyl]-1H-indol-2-yl}-phenyl-Ester (26)

Compound 26 was prepared according to the procedure of Example 25, as a foam. IR (KBr) 3410, 2920, 1750 cm$^{-1}$; MS 555.

EXAMPLE 10

2,3,4-Triacetyl-{1-O-[4-(2-piperidin-1-yl-ethoxy)-benzyl]-2-[4-(2, 2-dimethyl-propionyloxy)-phenyl]-3-methyl-1H-indol-5-yl}-glucuronic Acid Methyl Ester (27)

To a mixture of the 5-hydroxyindole cpd 25 (31.2 g, 0.058 mol, 1 eq), trichloroacetimidate D [150607-95-7](33.2 g, 0.069 mol, 1.2 eq) and molecular sieves (3 A, 28 g) in $CH_2Cl_2$ (0.5 L) was added $BF_3.OEt_2$ (16.5 g, 0.116 mol, 2 eq) dropwise at 0° C. The mixture was stirred at rt for 24 h. The mixture was filtered, quenched with conc. aq. $NaHCO_3$ (1 L), the organic layer was washed with water, brine, dried over $Na_2SO_4$ and evaporated to give 50.7 g of a yellow foam. The material was chromatographed on silica gel (2 Kg, column d=15 cm, eluant $EtOAc/Et_3N$ 9:1, 100 mL/3min, 125 mL fractions) to yield the desired product 27 as a foam. $^1$H NMR (DMSO) 7.42 (d, 2 H, J=8.5 Hz), 7.31 (d, 1 H, J=8.9 Hz), 7.23 (d, 2 H, J=8.5 Hz), 7.18 (d, 1 H, J=2.2 Hz), 6.82 (dd, 1 H, J=8.8 Hz, 2.3 Hz), 6.79–6.68 (m,4 H), 5.59 (d, 1 H, J=8.0 Hz), 5.47 (t, 1 H, J=9.6 Hz), 5.20 (s, 2 H), 5.15–5.03 (m, 2 H), 4.67(d, 1 H, J=9.9 Hz), 3.94 (t,2H, J=5.9 Hz), 3.65 (s,3 H), 2.58(t, 2 H, J=5.7 Hz), 2.43–2.35 (m, 4 H), 2.18 (s, 3 H), 2.06 (s, 3 H), 2.01 (s, 3 H), 2.00 (s, 3 H), 1.51–1.42 (m, 4 H), 1.32 (s, 11 H); IR (KBr) 2910, 1752 cm$^{-1}$; MS 857 (M+H$^+$).

EXAMPLE 11

2,3,4-Triacetyl-{1O-[4-(2-azepan-1-yl-ethoxy)-benzyl]-2-[4-(2,2-dimethyl-propionyloxy)-phenyl]-3-methyl-1H-indol-5-yl}-glucuronic Acid Methyl Ester (28)

The same procedure used for the preparation of compound 27 supra was used for compound 28. Purification via $SiO_2$, eluted with (20:1) $CHCl_3:CH_3OH$ gave 1.2 g, 82% of glycoside 6 as a brown foam. $R_f$=0.21 (20:1 $CHCl_3:CH_3OH$); $^1$H NMR (CDCl$_3$) 6.6–7.4 (m, 11H), 5.0–5.4 (m, 6H), 4.0–4.2 (m, 3H), 3.8 (s, 3H), 2.8–3.2 (m, 6H), 2.2 (s, 3H), 2.0–2.2 (m, 9H), 1.4–1.8 (m, 8H), 1.4 (s, 9H); $^{13}$C NMR (CDCl$_3$) 176.9, 170.1, 170.0, 169.9, 169.6, 169.3, 169.2, 168.5, 167.0, 157.6, 151.1, 150.8, 138.1, 133.7, 131.3, 130.4, 129.1, 128.9, 127.1, 121.5, 114.6, 113.7, 110.7, 109.2, 107.2, 101.1, 90.2, 72.6, 72.1, 71.7, 71.0, 69.7, 69.3, 67.8, 65.5, 56.0, 55.5, 52.8, 52.6, 47.1, 39.1, 27.0, 26.9, 26.6, 20.6, 20.5, 20.4, 9.3; LC/MS (ESI) retention time=15.9, M+H$^+$=871.4.

EXAMPLE 12

1-[4-(2-Piperidin-1-yl-ethoxy)-benzyl]-2-(4-hydroxy-phenyl)-3-methyl-1H-indol-5-ol 5-O-glucuronide triethylammonium salt (29)

A solution consisting of indole precursor 27 (29.8 g, 0.0385 mol) in dioxane/MeOH/H$_2$O (200 mL/100 mL/100 mL) and LiOH.H$_2$O (12.95 g, 0.31 mol, 8 eq) was stirred at 60° C. for 2 h. AcOH (18.5 mL) was added and the mixture was evaporated to give 53.6 g of the crude solid. The material was slurried with water (500 mL) for 2 h, filtered, washed with water, and dried to give 24.1 g of the crude product. This material was dissolved in MeOH/Et$_3$N (100 mL/5.3 mL) and ether (2L) was used to precipitate the salt as a white solid which was filtered, washed with ether and dried under vacuum to give 29 (27 g, 99%): $^1$H NMR (DMSO-d$_6$) δ 6.99 (m, 11 H), 5.11 (br s, 1H), 5.00 (d, 1 H, J=1.5 Hz), 3.99 (t, 2 H), 3.66 (d, 1 H, J=1.5 Hz), 3.26 (m,2 H), 2.92 (q, 6 H), 2.74 (t, 2 H), 2.52 (br s, 4 H), 2.1 (s, 3 H), 1.50 (br s, 4 H), 1.37 (br s, 2 H), 1.08 (t, 9 H).

EXAMPLE 13

1-[4-(2-Azepan-1-yl-ethoxy)-benzyl]-2-(4-hydroxy-phenyl)-3-methyl-1H-indol-5-ol 5-O-glucuronide (30)

To a solution of indole glycoside precursor 28 (2.8 g, 3.3 mmol) in (2:1:1) p-dioxane:MeOH:H$_2$O (52 mL) was added solid LiOH.H$_2$O (1.5 g, 36 mmol) at rt under Ar. The suspension was heated to 65° C. After 1.5 h, glacial acetic acid (1.5 mL) was added. The reaction mixture was concentrated in vacuo. Purification via SiO$_2$, eluted with (20:1:2) CH$_3$CN:HOAc:H$_2$O followed by (10:1:2) CH$_3$CN:HOAc:H$_2$O gave a brown syrup. Addition of H$_2$O (30 mL) followed by MeOH (10 mL) to the brown syrup gave an light brown suspension. This was filtered and air-dried to give 840 mg, 40% of glucuronide 30 as a light brown solid. R$_f$=0.24 (10:1:2 CH$_3$CN:HOAc:H$_2$O); HPLC retention time=23.2 min with 95 area %, at 220 nm; $^1$H NMR (DMSO) 6.8–7.2 (m, 7H), 6.7 (s, 4H), 5.1 (br s, OH), 4.8 (d, 1H, J=5.5 Hz), 3.9 (t, 2H, J=4.5 Hz), 3.1–3.6 (m, 8H), 2.77 (t, 2H, J=4.5 Hz), 2.5–2.7 (m, 4H), 2.1 (s, 3H), 1.5 (s, 8H); $^{13}$C NMR (DMSO) 172.3, 157.5, 157.4, 151.7, 138.5, 132.2, 131.3, 130.4, 128.6, 127.2, 121.7, 115.4, 114.3, 112.9, 110.5, 107.2, 105.6, 102.3, 76.6, 73.9, 73.3, 72.1, 66.1, 56.0, 55.1, 40.1, 39.9, 39.7, 39.5, 39.3, 39.1, 38.9, 27.8, 26.5, 9.4; IR (KBr): ν$_{max}$ 3424, 2928, 1612, 1510, 1475, 1444, 1238, 1099, 1065, 1039, 1020, 917, 840 cm$^{-1}$; LC/MS (ESI) retention time=9.0, M+H$^+$=647.3.

EXAMPLE 14

4-{5-Benzyloxy-3-methyl-1-[4-(2-piperidin-1-yl-ethoxy)-benzyl]-1H-indol-2-yl}-phenol (31)

A mixture of the substituted indole 23 (61.8 g, 0.098 mol, 1 eq) and LiOH.H$_2$O (8.5 g, 0.202 mol, 2.1 eq) in dioxane/MeOH/H$_2$O (300 mL, 150 mL, 150 mL) was stirred at 60° C. for 2 h. The mixture was cooled to rt and 12.1 mL of AcOH was added in order to adjust the pH to approximately 7. Then water (600 mL) was added and the mixture was extracted with CH$_2$Cl$_2$ (6×150 mL), the organic phase was washed with conc. Aq. Na$_2$CO$_3$, H$_2$O, brine, dried over Na$_2$SO$_4$, and evaporated to give 31 (51.6 g, 97%) as a yellow foam: $^1$H NMR (CDCl$_3$) δ 7.07 (m, 19 H), 6.10 (s, 2 H), 5.03 (s, 2 H), 4.03 (t, 2 H), 2.8 (t, 2 H), 2.53 (br s, 4 H), 2.21 (s, 3 H), 1.63 (t, 4 H), 1.43 (br s, 2 H).

EXAMPLE 15

4-{5-Benzyloxy-3-methyl-1-[4-(2-azepan-1-yl-ethoxy)-benzyl]-1H-indol-2-yl}-phenol (32)

Compound 32 was synthesized analogously to compound 31: $^1$H NMR (DMSO) δ 9.83 (br s, 1 H), 7.49–7.29 (m, 5 H), 7.21–7.09 (m, 4 H), 6.89–6.73 (m, 7 H), 5.15 (s, 2 H), 5.11 (s, 2 H), 4.04 (t, 2 H, J=7.1 Hz), 2.77 (t, 2 H, J=6.0 Hz), 2.65–2.60 (m, 4 H), 2.15 (s, 3 H), 1.51 (br s, 8 H).

EXAMPLE 16

2,3,4-O-Triacetyl-1-O-(4-{5-benzyloxy-3-methyl-1-[4-(2-piperidin-1-yl-ethoxy)-benzyl]-1H-indol-2-yl}-phenyl)-beta-D-glucuronic Acid Methyl Ester (33)

To a mixture of indole 31 (35.6 g, 0.065 mol, 1 eq), trichloroacetimidate D [150607-95-7](37.4 g, 0.078 mol, 1.3 eq) and molecular sieves (3A, 28 g) in $CH_2Cl_2$ (500 mL) was added $BF_3 \cdot OEt_2$ (18.45 g, 0.13 mol, 2 eq) dropwise at 0° C. The mixture was stirred at rt for 48 h. The mixture was filtered and then quenched with conc. aq. $NaHCO_3$ (1 L), the organic layer was washed with water, brine, dried over $Na_2SO_4$ and evaporated to give 65.4 g of a yellow foam. The foam was flash chromatographed on silica gel (2 Kg, column d=15 cm) using $EtOAc/Et_3N$ (9:1) to yield 33 (34.5 g, 59%) of the desired compound: MS 863 ($M+H^+$).

EXAMPLE 17

2,3,4-O-Triacetyl-1-O-(4-{5-benzyloxy-3-methyl-1-[4-(2-azepan-1-yl-ethoxy)-benzyl]-1H-indol-2-yl}-phenyl)-beta-D-glucuronic Acid Methyl Ester (34)

Compound was prepared in a similar fashion to that described for 33 supra: $R_f$=0.21 (20:1 $CHCl_3$:$CH_3OH$); $^1H$ NMR ($CDCl_3$) 6.6–7.7 (m, 16 H), 5.1–5.5 (m, 8H), 4.2–4.4 (m, 3H), 3.8 (s, 3H), 3.0–3.4 (m, 6H), 2.23 (s, 3H), 2.0–2.2 (m, 8H), 1.9 (m, 4H), 1.7 (m, 4H); $^{13}C$ NMR ($CDCl_3$) 170.1, 169.4, 169.3, 166.9, 156.9, 156.3, 153.3, 137.7, 132.2, 131.8, 131.4, 128.5, 127.7, 127.6, 127.3, 116.9, 114.7, 112.6, 110.9, 108.8, 102.5, 98.9, 72.7, 71.8, 71.1, 71.0, 69.1, 64.1, 55.9, 55.2, 53.0, 47.0, 26.9, 24.8, 20.6, 20.5, 20.4, 9.5; IR (KBr): $v_{max}$ 3435, 2934, 2862, 1756, 1612, 1510, 1372, 1226, 1176, 1041, 828 $cm^{-1}$; LC/MS (ESI) retention time= 16.1, $M+H^+$=877.

EXAMPLE 18

2,3,4-O-Triacetyl-1-O-(4-{5-hydroxy-3-methyl-1-[4-(2-piperidin-1-yl-ethoxy)-benzyl]-1H-indol-2-yl}-phenyl)-beta-D-glucuronic Acid Methyl Ester (35)

Glycosidated indole 33 (34 g, 0.039 mol) in 400 mL THF/MeOH (1:1) was treated with 10% Pd/C (5.4 g) and hydrogenated in a Parr apparatus at 50 psi for 30 h. The mixture was filtered through Siluflock and 0.34 g of L-Ascorbic acid was added to the filtrate. The cake of Siluflock was washed with THF and the combined filtrates were concentrated to yield product 35 (29.8 g, 98%) as a yellowish-white solid: $^1H$ NMR ($CDCl_3$) δ 6.95 (m, 11 H), 5.34 (m, 2 H), 5.14 (d, 1 H, J=2 Hz), 5.01 (s, 2 H), 4.21 (m, 1 H), 4.06 (t, 2 H), 2.83 (t, 2 H), 2.62 (br s, 4 H), 2.13 (s, 3 H), 1.65 (t, 4 H), 1.44 (br s, 2 H).

EXAMPLE 19

2,3,4-O-Triacetyl-1-O-(4-{5-hydroxy-3-methyl-1-[4-(2-azepan-1-yl-ethoxy)-benzyl]-1H-indol-2-yl}-phenyl)-beta-D-glucuronic Acid Methyl Ester (36)

Glycosidated indole 34 (3.7 g, 4.2 mmol) in 60 mL THF/MeOH (1:1) was treated with 10% Pd/C (1.5 g) and hydrogenated in a Parr apparatus at 40 psi for 23 h. The reaction mixture was filtered through a bed of Celite and the filter cake was washed with THF (20 mL) and EtOH (20 mL). To avoid any air oxidation, L-ascorbic acid (0.37 g) was added to the filtered solution. The solution was concentrated and chromatographed on silica gel using $CHCl_3$/i-PrOH (7:1) to render the product 35 (1.6 g, 48%) as a brown foam: $R_f$=0.20 (7:1 $CHCl_3$:iPrOH); $^1H$ NMR (DMSO) 6.5–7.5 (m, 11H), 5.7 (d, 1H, J=7.9 Hz), 5.5 (t, 1H, J=9.6 Hz), 4.9–5.2 (m, 4H), 4.7 (d, 1H, J=9.9 Hz), 3.6 (s, 3H), 3.3 (s, 8H), 2.1 (s, 3H), 1.9–2.2 (m, 9H), 1.5–1.9 (m, 8H); $^{13}C$ NMR ($CDCl_3$) 170.0, 169.0, 167.0, 157.0, 156.5, 150.0, 138.0, 131.7, 131.6, 130.0, 127.3, 116.9, 114.7, 112.0, 111.0, 108.0, 104.5, 98.8, 72.6, 71.8, 71.1, 69.1, 64.4, 55.0, 55.2, 53.0, 47.0, 26.7, 23.6, 20.6, 20.5, 9.5; IR (KBr): $v_{max}$ 3427, 3037, 2935, 2612, 1757, 1612, 1510, 1462, 1374, 1227, 1040 $cm^{-1}$; LC/MS (ESI) retention time=13.0, $M+H^+$=787.

EXAMPLE 20

2-(4-Hydroxy-phenyl)-3-methyl-1-[4-(2-piperidin-1-yl-ethoxy)-benzyl]-1H-indol-5-ol 4-O-Glucuronide Triethyl Ammonium Salt (37)

Glycosidated indole 35 (25 g, 0.029 mol, 1 eq) and $LiOH \cdot H_2O$ (12.3 g, 0.29 mol, 10 eq) in 300 ml of dioxane/$MeOH/H_2O$ (2/1/1) was stirred at 60° C. for 2 h. The mixture was allowed to cool to rt and AcOH (13.5 mL) was added. The solution was concentrated to yield 44.3 g of a yellow foam. This foam was washed with water and the residue dried and then dissolved in 160 mL of $MeOH/Et_3N$ (15/1) and the resultant solution concentrated to give the crude material which was redissolved in MeOH (100 mL) at 40° C. and a white precipitate fell out of solution almost immediately. The precipitate was filtered, washed with MeOH and dried under vacuum to render 9.7 g of 37 (78%) as a white solid: $^1H$ NMR (DMSO) δ 7.16 (m, 4 H), 6.86 (d, 2 H, J=2.8 Hz), 6.81 (m, 1 H), 6.74 (s, 4 H), 5.15 (s, 2 H), 4.90 (d, 1 H, J=2.0 Hz), 3.98 (m, 2 H), 3.70 (d, 1 H, J=2.0 Hz), 3.32 (m, 3 H), 2.78 (t, 2 H), 2.58 (br s, 4 H), 2.14 (s, 3 H), 1.51 (br s, 4 H), 1.38 (br s, 2 H).

EXAMPLE 21

1-[4-(2-Azepan-1-yl-ethoxy)-benzyl]-2-(4-hydroxy-phenyl)-3-methyl-1H-indol-5-ol 4-O-glucuronide (38)

To a solution of the indole glycoside 36 (2.8 g, 3.3 mmol) in (2:1:1) dioxane:MeOH:$H_2O$ (52 mL) was added solid $LiOH \cdot H_2O$ (1.5 g, 36 mmol) at rt under Ar. The suspension was heated to 65° C. After 1.5 h, glacial acetic acid (1.5 mL) was added. The reaction mixture was concentrated in vacuo. Purification via $SiO_2$, eluted with (20:1:2) $CH_3CN$:HOAc:$H_2O$ followed by (10:1:2) $CH_3CN$:HOAc:$H_2O$ gave a brown syrup. Addition of $H_2O$ (30 mL) followed by MeOH (10 mL) to the brown syrup gave an light brown suspension. This was filtered and air-dried to give 840 mg, 40% of glucuronide 38 as a light brown solid. $R_f$=0.24 (10:1:2 $CH_3CN$:HOAc:$H_2O$); HPLC retention time=23.2 min with 95 area %, at 220 nm; $^1H$ NMR (DMSO) 6.8–7.2 (m, 7H), 6.7 (s, 4H), 5.1 (br s, OH), 4.8 (d, 1H, J=5.5 Hz), 3.9 (t, 2H, J=4.5 Hz), 3.1–3.6 (m, 8H), 2.77 (t, 2H, J=4.5 Hz), 2.5–2.7 (m, 4H), 2.1 (s, 3H), 1.5 (s, 8H); $^{13}C$ NMR (DMSO) 172.3, 157.5, 157.4, 151.7, 138.5, 132.2, 131.3, 130.4, 128.6, 127.2, 121.7, 115.4, 114.3, 112.9, 110.5, 107.2, 105.6, 102.3, 76.6, 73.9, 73.3, 72.1, 66.1, 56.0, 55.1, 40.1, 39.9, 39.7, 39.5, 39.3, 39.1, 38.9, 27.8, 26.5, 9.4; IR (KBr): $v_{max}$ 3424, 2928, 1612, 1510, 1475, 1444, 1238, 1099, 1065, 1039, 1020, 917, 840 $cm^{-1}$; LC/MS (ESI) retention time=9.0, $M+H^+$=647.3.

The bis-glucuronide, compounds 46 and 47 [Examples 22–26], were prepared according to Scheme 7 as shown below.

Scheme 7

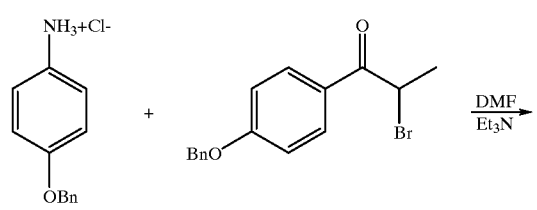

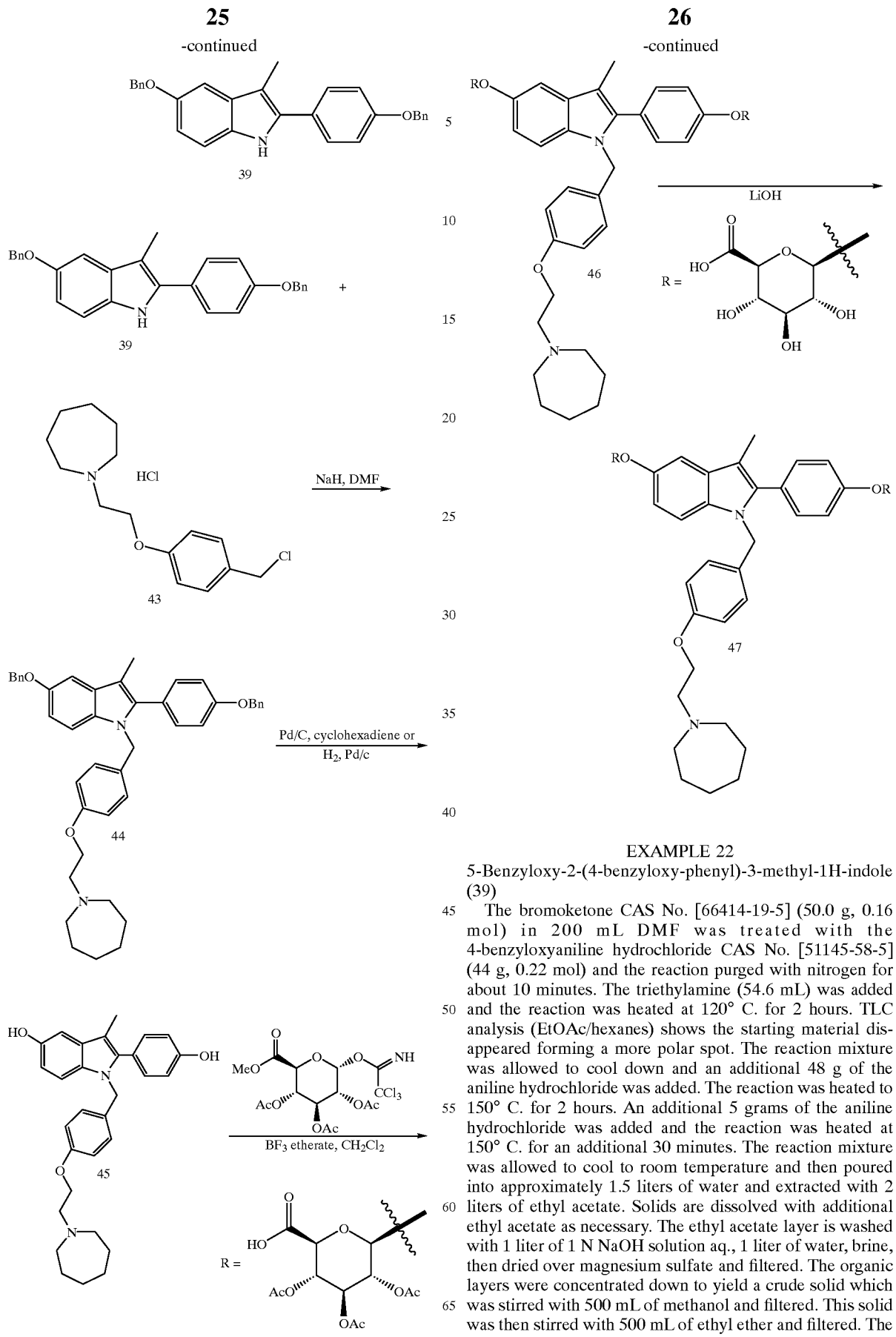

EXAMPLE 22
5-Benzyloxy-2-(4-benzyloxy-phenyl)-3-methyl-1H-indole (39)

The bromoketone CAS No. [66414-19-5] (50.0 g, 0.16 mol) in 200 mL DMF was treated with the 4-benzyloxyaniline hydrochloride CAS No. [51145-58-5] (44 g, 0.22 mol) and the reaction purged with nitrogen for about 10 minutes. The triethylamine (54.6 mL) was added and the reaction was heated at 120° C. for 2 hours. TLC analysis (EtOAc/hexanes) shows the starting material disappeared forming a more polar spot. The reaction mixture was allowed to cool down and an additional 48 g of the aniline hydrochloride was added. The reaction was heated to 150° C. for 2 hours. An additional 5 grams of the aniline hydrochloride was added and the reaction was heated at 150° C. for an additional 30 minutes. The reaction mixture was allowed to cool to room temperature and then poured into approximately 1.5 liters of water and extracted with 2 liters of ethyl acetate. Solids are dissolved with additional ethyl acetate as necessary. The ethyl acetate layer is washed with 1 liter of 1 N NaOH solution aq., 1 liter of water, brine, then dried over magnesium sulfate and filtered. The organic layers were concentrated down to yield a crude solid which was stirred with 500 mL of methanol and filtered. This solid was then stirred with 500 mL of ethyl ether and filtered. The solid was stirred alternatively with methanol and ether until it is of whitish color. Reaction yields 36 g of product: Mp=150–152° C.; $^1$H NMR (DMSO) δ 10.88 (s, 1 H), 7.56 (d, 2 H, J=8.8 Hz), 7.48 (d, 4 H, J=7.9 Hz), 7.42–7.29 (m, 6 H), 7.21 (d, 1 H, J=7.0 Hz), 7.13 (d, 2 H, J=8.8 Hz), 7.08 (d, 1 H, J=2.2 Hz), 6.94 (dd, 1 H, J=8.8, 2.4 Hz), 5.16 (s, 2 H), 5.11 (s, 2 H), 2.33 (s, 3 H); IR (KBr) 3470, 2880, 2820, 1620 cm$^{-1}$; MS eI m/z 419.

EXAMPLE 23

5-Benzyloxy-2-(4-benzyloxy-phenyl)-3-methyl-1-[4-(2-azopan-1-yl-ethoxy)-benzyl]-1H-indole (44)

To a slurry of NaH (20.0 g, 60% oil dispersion, 0.5 mol, 2.5 eq.) solution of 5-Benzyloxy-2-(4-benzyloxy-phenyl)-3-methyl-1H-indole (84 g, 0.2 mol, 1.0 eq.) in DMF (100 mL) was added at 0/+10° C. over 1 h. The reaction mixture was stirred for 30 min. A solution of the benzylchloride (synthesis shown in scheme 7 and details given in the following experimental) (67 g, 0.22 mol, 1.1 eq.) in DME (200 mL) was added dropwise at 0/+10° C. over 2 h. The reaction mixture was stirred at 25° C. for 2 h. TLC at this point showed no starting material, mostly product (EtOAc/hexane 1:5). The reaction mixture was diluted with water (1 L), extracted with EtOAc (3×1 L), and dried over MgSO$_4$. The solution was concentrated to 150 mL, poured in MeOH (750 mL), and stirred overnight. The precipitate was filtered and dried to give the title compound (99 g, 76%): Mp=106–107° C.; $^1$H NMR (DMSO) δ 7.47 (d, 4 H, J=8.3 Hz), 7.41–7.36 (m, 4 H), 7.36–7.30 (m, 2 H), 7.29 (d, 2 H, J=8.8 Hz), 7.19 (d, 1 H, J=8.8 Hz), 7.14–7.10 (m, 3 H), 6.80 (dd, 1 H, J=8.8 Hz), 6.73 (s, 4 H), 5.15 (s, 2 H), 5.13 (s, 2 H), 5.11 (s, 2 H), 3.90 (t, 2 H, J=5.9 Hz), 2.76 (t, 2 H, J=5.9 Hz), 2.64–2.56 (m, 4 H), 2.15 (s, 3 H), 1.58–1.44 (m, 8 H); MS FAB m/z 651 (M+H+).

EXAMPLE 24

1-[4-(2-Azepan-1-yl-ethoxy)-benzyl]-2-(4-hydroxy-phenyl)-3-methyl-1H-indol-5-ol (45)

A solution consisting of indole 44 (17.5 g, 26.9 mmol) in THF/EtOH (1:1) was hydrogenated under an atmosphere of H$_2$ using 10% Pd/C as a catalyst. Chromatography on silica gel CH$_2$Cl$_2$/MeOH (gradient from 100/0 to 85/15) yields the desired product as 8.5 g of white foam along with 2.5 g of a fraction containing small impurities. Although the free base is the material used in the next step (bis-glucuronidation), for purposes of characterization and enhancing the compounds shelf life an acid addition salt may be made with HCl by dissolving the compound in MeOH and treating with 1.1 eq of a 2 N aq HCl solution. The compound slowly precipitates out as white crystals. Physical data listed below describes the HCl salt of indole 45:

Mp=172–174° C.; $^1$H NMR (DMSO) 10.11 (br s, 1 H), 9.70 (s, 1 H), 8.71 (s, 1 H); 7.15 (d, 2 H, J=8.6 Hz), 7.05 (d, 1 H, J=8.8 Hz), 6.85 (d, 2 H, J=8.8 Hz), 6.80–6.77 (m, 5 H), 6.56 (dd, 1 H, J=8.8 Hz, 2.2 Hz), 5.11 (s, 2 H), 4.26 (t, 2 H, J=4.6 Hz), 3.48–3.30 (m, 4 H), 3.22–3.08 (m, 2 H), 2.09 (s, 3 H), 1.83–1.76 (m, 4 H), 1.67–1.48 (m, 4 H); IR (KBr) 3500 br, 3250 br, 2900, 1610; MS FAB m/z 471 (M+H$^+$).

EXAMPLE 25

2,3,4-O-Triacetyl-1-O-[4-[1-[4-[2-(hexahydro-1H-azepin-1-yl)ethoxy]benzyl]-3-methyl-5-[(2,3,4-O-triacaetyl-6-O-methyl-beta-D-glucopyranuronylosyl)oxyl-1H-indol-2-yl]phenyl]-beta-D-glucopyranosiduronic Acid Methyl Ester (46)

A mixture consisting of the bis-phenolic indole 45 (2.5 g, 5.3 mmol) and the glucuronyl imnidate D (5.60 g, 11.7 mmol, 2.2 eq) in CH$_2$Cl$_2$ (25 mL) was treated with slow addition of the BF$_3$.OEt$_2$ (1.43 mL, 11.7 mmol, 2.2 eq) while stirring the reaction mixture vigorously. After the addition, the reaction was heated to reflux for 2.5 h. Some of the starting material remained stuck to the bottom of the flask throughout the reaction. The reaction was worked-up by adding additional CH$_2$Cl$_2$, and a small amount of MeOH and washing the organic layer with water, brine and drying over MgSO$_4$. The crude material was purified by chromatography on silica gel with CH$_2$Cl$_2$/MeOH (95/5) to yield the protected bis-glucuronide 46 (0.95 g): Mp=110–116° C.; $^1$H NMR (DMSO-d$_6$) δ 7.36 (d, 2 H, J=8.5 Hz), 7.25 (d, 1 H, J=8.8 Hz), 7.16–7.10 (m, 3 H), 6.79 (dd, 1 H, J=8.9Hz, 2.0 Hz), 6.75 (br s, 4 H), 5.74 (d, 1 H, J=7.7 Hz), 5.58 (d, 1 H, J=8.0 Hz), 5.47 (dt, 2 H, J=9.5 Hz, 2.3 Hz), 5.18 (br s, 2 H), 5.15–5.04 (m, 4 H), 4.73 (d, 1 H, J=9.9 Hz), 4.66 (d, 1 H, J=10.0 Hz), 3.93 (t, 2 H, J=5.8 Hz), 3.64 (s, 3 H), 3.636 (s, 3 H), 2.81–2.60 (m, 6 H), 2.16 (s, 3 H), 2.05 (s, 3 H), 2.03 (s, 3 H), 2.02 (s, 3 H), 2.00 (br s, 9 H), 1.61–1.47 (m, 8 H); MS 1103.7 (M+H$^+$).

EXAMPLE 26

4-[5-(beta-D-Glucopyranuronosyloxy)-1-[4-[2-(hexahydro-1H-azepin-1-yl)ethoxy]benzyl]-3-methyl-1H-indol-2-yl]phenyl-beta-D-Flucopyranosiduronic Acid (47)

The protected indole bis-glucuronide 46 (0.89 g, 0.81 mmol, 1 eq) was dissolved in 24 mL of p-dioxane/MeOH (5/1) and treated with a slow addition of 24 mL of an aqueous LiOH (0.31 g, 12.9 mmol, 12 eq) solution. The reaction was heated to 60° C. for 2 h. After allowing the reaction to come to rt, AcOH was added (0.97 g, 16.1 mmol, 20 eq) and the solution concentrated under reduced pressure. Benzene was added and this process repeated a couple of times in order to azeotrope any residual water from the reaction mixture. The crude residue was purified by reverse phase HPLC to yield the desired product 47 (0.294 g): $^1$H NMR (DMSO-d$_6$) δ 7.31 (d, 1 H, J=8.8 Hz), 7.22 (d, 2 H, J=8.5 Hz), 7.19 (br s, 1H), 7.09 (d, 2 H, J=8.4 Hz), 6.90 (d, 1 H, J=8.7 Hz), 6.75–6.64 (m, 4 H), 5.45–5.35 (m, 2 H), 5.28–5.10 (m,4 H), 4.99–4.93 (m, 2 H), 4.87–4.83 (m, 2 H), 4.10–3.00 (several protons buried under H$_2$O peak), 2.13 (s, 3 H), 1.70 (br s, 4 H), 1.56 (br s, 4 H); MS 823 (M+H$^+$).

The preparation of side chain 22 is shown in Scheme 8, as provided below. Side chain 21 was prepared analogously.

Scheme 8

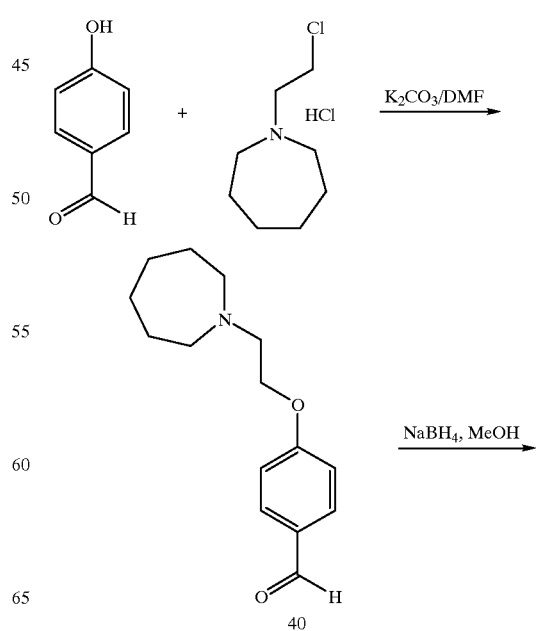

40

-continued

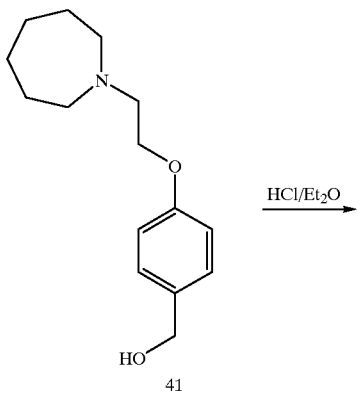

EXAMPLE 27
4-(2-hexamethyleneimine-1-yl-ethoxy)-benzyl Aldehyde (40)

To a well-stirred slurry of NaH (65 g, 60% oil dispersion, 1.6 mol, 2.2 eq.) in DME (500 mL) a solution of p-hydroxybenzaldehyde hydrochloride (90 g, 0.74 mol, 1.0 eq.) is added dropwise at 0° C. The reaction mixture is stirred for 30 min, then 4-[2-(hexamethyleneimino)]ethylchloride (153 g, 0.77 mol, 1.0 eq.) is added in portions. The reaction mixture is stirred for 1 h. TLC at this point shows little starting material, mostly product (EtOAc/hexane 1:1). The reaction mixture is diluted with water (1 L), and extracted with ether (5 L). The organic layer is dried over MgSO$_4$, and concentrated on a rotary evaporator to give 176.8 g (97%) of aldehyde 40 as a yellow oil.

$^1$H NMR (CDCl$_3$/TMS): δ 9.87 (s, 1H), 7.81 (d, 2H, J=8.7 Hz), 7.02 (d, 2H, J=8.7 Hz), 4.14 (t, 2H, J=6.09 Hz), 2.98 (t, 2H, J=6.14 Hz), 2.78 (m, 4H), 1.66–1.61 (m, 8H).

EXAMPLE 28
4-(2-hexamethyleneimine-1-yl-ethoxy)-benzyl Alcohol (41)

To a stirred solution of the aldehyde 40 (200 g, 0.72 mol, 1.0 eq.) in methanol (400 mL) at 0/+5° C. sodium borohydride (15.6 g, 0.41 mol, 0.57 eq.) is added in portions. The reaction is stirred for 30 min. TLC at this point shows no starting material, mostly product (EtOAc/hexane/triethylamine 3:7:1). The reaction mixture is diluted with water (400 mL), extracted with methylene chloride (3×400 mL), and dried over MgSO$_4$. The solution is concentrated on a rotary evaporator to give 201 g (100%) of the alcohol 41 as a thick oil: $^1$H NMR (CDCl$_3$/TMS): 7.27 (d, 2H, J=8.5 Hz), 6.87 (d, 2H, J=8.5 Hz), 4.60 (s, 2H), 4.05 (t, 2H, J=6.21 Hz), 2.93 (t, 2H, J=6.15 Hz), 2.77 (m, 4H), 1.7–1.5 (m, 8H).

EXAMPLE 29
(4-Chloromethyl-phenoxy)-ethyl-hexamethyleneimine-1-yl Hydrochloride (22)

To a solution of the alcohol 41 (179 g, 0.72 mol, 1 eq.) in THF (300 mL) a solution of HCl (26.3 g of HCl in 263 mL of THF, 0.72 mol, 1.0 eq.) is added dropwise at 0/+10° C. A white precipitate is formed. Thionyl chloride (80 mL, 1.1 mol, 1.5 eq.) is added to the thick slurry of the hydrochloride 42, and the mixture is heated to 50° C. until clear. The reaction mixture is concentrated to 350 mL, and kept in refrigerator overnight. The white solid obtained is filtered, washed with cold THF (100 mL), and dried to give 147 g (67%) of chloride 22: $^1$H NMR (DMSO-d$_6$): 11 (br s, HCl), 7.40 (d, 2H, J=8.6 Hz), 7.00 (d, 2H, J=8.6 Hz), 4.74 (s, 2H), 4.44 (t, 2H, J=5.25), 3.64–3.39 (m, 4H), 3.25–3.17 (m, 2H), 1.84–1.54 (m, 8H).

EXAMPLE 30
(4-Chloromethyl-phenoxy)-ethyl-piperidin-1-yl Hydrochloride (21)

The side chain 21 was prepared analogously to side chain 22 described supra: $^1$H NMR (DMSO-d$_6$): 11 (br s, HCl), 7.39 (d, 2H, J=8.5 Hz), 6.99 (d, 2H, J=8.5 Hz), 4.74 (s, 211), 4.46 (m, 2H), 3.45 (m, 4H), 2.69 (m, 2H) and 1.9–1.2 (m, 6H).

What is claimed is:

1. A compound of formula I having the structure

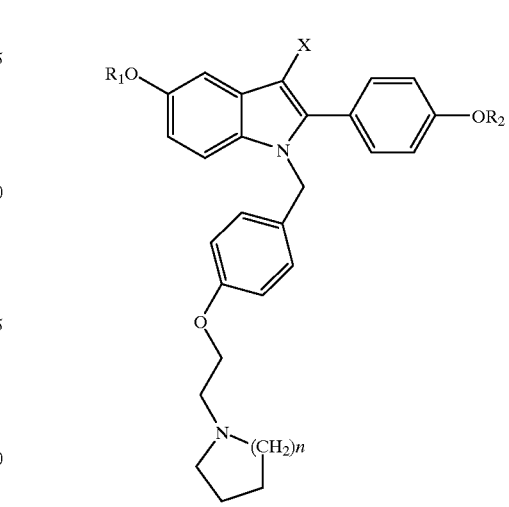

wherein:
R$_1$ and R$_2$ are independently, hydrogen, alkyl chain of 1–6 carbon atoms, benzyl, acyl of 2–7 carbon atoms, benzoyl,

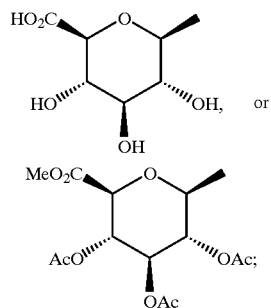

X is hydrogen, alkyl of 1–6 carbon atoms, CN, halogen, trifluoromethyl, or thioalkyl of 1–6 carbon atoms;

n=1–3;

with the proviso that at least one of $R_1$ or $R_2$ are not hydrogen, alkyl chain of 1–6 carbon atoms, benzyl, acyl of 2–7 carbon atoms, or benzoyl;

or a pharmaceutically acceptable salt thereof.

2. The compound according to claim 1, which is 2,3,4-triacetyl-{1-O-[4-(2-piperidin-1-yl-ethoxy)-benzyl]-2-[4-(2,2-dimethyl-propionyloxy)-phenyl]-3-methyl-1H-indol-5-yl}-glucuronic acid methyl ester or a pharmaceutically acceptable salt thereof.

3. The compound according to claim 1, which is 2,3,4-triacetyl-{1-O-[4-(2-azepan-1-yl-ethoxy)-benzyl]-2-[4-(2,2-dimethyl-propionyloxy)-phenyl]-3-methyl-1H-indol-5-yl}-glucuronic acid methyl ester or a pharmaceutically acceptable salt thereof.

4. The compound according to claim 1, which is 1-[4-(2-piperidin-1-yl-ethoxy)-benzyl]-2-(4-hydroxy-phenyl)-3-methyl-1H-indol-5-ol 5-O-glucuronide triethylammonium salt.

5. The compound according to claim 1, which is 1-[4-(2-Azepan-1-yl-ethoxy)-benzyl]-2-(4-hydroxy-phenyl)-3-methyl-1H-indol-5-ol 5-O-glucuronide or a pharmaceutically acceptable salt thereof.

6. The compound according to claim 1, which is 2,3,4-O-triacetyl-1-O-(4-{5-benzyloxy-3-methyl-1-[4-(2-piperidin-1-yl-ethoxy)-benzyl]-1H-indol-2-yl}-phenyl)-beta-D-glucuronic acid methyl ester or a pharmaceutically acceptable salt thereof.

7. The compound according to claim 1, which is 2,3,4-O-triacetyl-1-O-(4-{5-benzyloxy-3-methyl-1-[4-(2-azepan-1-yl-ethoxy)-benzyl]-1H-indol-2-yl}-phenyl)-beta-D-glucuronic acid methyl ester or a pharmaceutically acceptable salt thereof.

8. The compound according to claim 1, which is 2,3,4-O-triacetyl-1-O-(4-{5-hydroxy-3-methyl-1-[4-(2-piperidin-1-yl-ethoxy)-benzyl]-1H-indol-2-yl }-phenyl)-beta-D-glucuronic acid methyl ester or a pharmaceutically acceptable salt thereof.

9. The compound according to claim 1, which is 2,3,4-O-triacetyl-1-O-(4-{5-hydroxy-3-methyl-1-[4-(2-azepan-1-yl-ethoxy)-benzyl]-1H-indol-2-yl}-phenyl)-beta-D-glucuronic acid methyl ester or a pharmaceutically acceptable salt thereof.

10. The compound according to claim 1, which is 2-(4-hydroxy-phenyl)-3-methyl-1-[4-(2-piperidin-1-yl-ethoxy)-benzyl]-1H-indol-5-ol 4-O-glucuronide or a pharmaceutically acceptable salt thereof.

11. The compound according to claim 1, which is 2-(4-Hydroxy-phenyl)-3-methyl-1-[4-(2-piperidin-1-yl-ethoxy)-benzyl]-1H-indol-5-ol 4-O-glucuronide triethyl ammonium salt.

12. The compound according to claim 1, which is 1-[4-(2-azepan-1-yl-ethoxy)-benzyl]-2-(4-hydroxy-phenyl)-3-methyl-1H-indol-5-ol 4-O-glucuronide or a pharmaceutically acceptable salt thereof.

13. The compound according to claim 1, which is 2,3,4-O-triacetyl-1-O-[4-[1-[4-[2-(hexahydro-1H-azepin-1-yl)ethoxy]benzyl]-3-methyl-5-[(2,3,4-O-triacaetyl-6-O-methyl-beta-D-glucopyranuronylosyl)oxy]-1H-indol-2-yl]phenyl]-beta-D-glucopyranosiduronic acid methyl ester or a pharmaceutically acceptable salt thereof.

14. The compound according to claim 1, which is 4-[5-(beta-D-glucopyranuronosyloxy)-1-[4-[2-(hexahydro-1H-azepin-1-yl)ethoxy]benzyl]-3-methyl-1H-indol-2-yl]phenyl-beta-D-glucopyranosiduronic acid.

15. A pharmaceutical composition, which comprises a compound of formula I having the structure

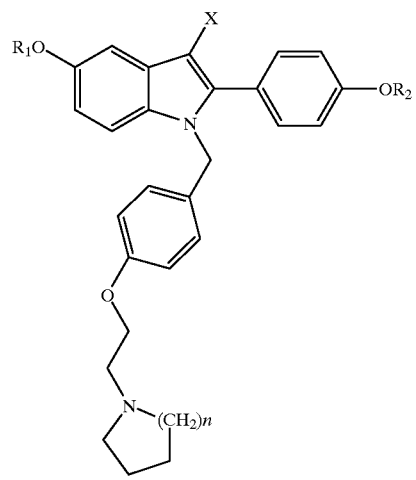

I wherein:

$R_1$ and $R_2$ are independently, hydrogen, alkyl chain of 1–6 carbon atoms, benzyl, acyl of 2–7 carbon atoms, benzoyl,

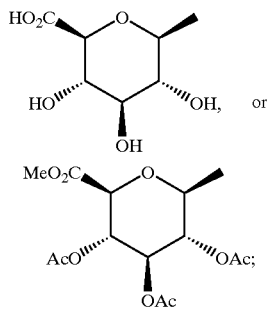

X is hydrogen, alkyl of 1–6 carbon atoms, CN, halogen, trifluoromethyl, or thioalkyl of 1–6 carbon atoms;

n=1–3;

with the proviso that at least one of $R_1$ or $R_2$ are not hydrogen, alkyl chain of 1–6 carbon atoms, benzyl, acyl of 2–7 carbon atoms, or benzoyl;

or a pharmaceutically acceptable salt thereof, and a pharmaceutical carrier.

* * * * *